(12) United States Patent
Straub

(10) Patent No.: US 8,901,311 B2
(45) Date of Patent: Dec. 2, 2014

(54) METHOD FOR PRODUCING HETEROCYCLIC FLUOROALKENYL SULFONES

(75) Inventor: Alexander Straub, Wuppertal (DE)

(73) Assignee: Makhteshim Chemical Works, Ltd., Beer Sheva (IL)

( * ) Notice: Subject to any disclaimer, the term of this patent is extended or adjusted under 35 U.S.C. 154(b) by 0 days.

(21) Appl. No.: 10/518,454

(22) PCT Filed: Jun. 20, 2003

(86) PCT No.: PCT/EP03/06511
§ 371 (c)(1),
(2), (4) Date: Aug. 1, 2005

(87) PCT Pub. No.: WO2004/005268
PCT Pub. Date: Jan. 15, 2004

(65) Prior Publication Data
US 2006/0004196 A1 Jan. 5, 2006

(30) Foreign Application Priority Data
Jul. 3, 2002 (DE) .................. 102 29 776

(51) Int. Cl.
*C07D 277/36* (2006.01)
(52) U.S. Cl.
CPC .................. *C07D 277/36* (2013.01)
USPC ....................................... 548/182
(58) Field of Classification Search
USPC ....................................... 548/182
See application file for complete search history.

(56) References Cited

U.S. PATENT DOCUMENTS

| | | | |
|---|---|---|---|
| 3,513,172 A | 5/1970 | Brokke | 260/302 |
| 3,697,538 A | 10/1972 | Boocock et al. | 260/309 |
| 5,274,139 A | 12/1993 | Drango et al. | |
| 5,705,516 A | 1/1998 | Tumbull et al. | 514/376 |
| 5,912,243 A | 6/1999 | Dowling et al. | 514/241 |
| 5,952,359 A | 9/1999 | Godfrey et al. | 514/369 |
| 5,965,737 A | 10/1999 | Prasad et al. | 548/136 |
| 6,025,497 A | 2/2000 | Bowden et al. | |
| 6,031,108 A | 2/2000 | Prasad et al. | 548/142 |
| 6,156,904 A | 12/2000 | Bowden et al. | |
| 6,710,045 B2 | 3/2004 | Kraatz et al. | |
| 6,734,198 B1 * | 5/2004 | Watanabe et al. | 514/369 |
| 6,908,937 B2 | 6/2005 | Kraatz et al. | |
| 6,916,938 B2 | 7/2005 | Oguma et al. | |
| 6,927,215 B2 | 8/2005 | Kraatz et al. | |
| 7,078,527 B2 | 7/2006 | Straub | |
| 2003/0207869 A1 | 11/2003 | Kraatz et al. | 514/226.8 |
| 2004/0106658 A1 | 6/2004 | Kraatz et al. | |
| 2004/0127525 A1 | 7/2004 | Kraatz et al. | 514/362 |
| 2005/0124816 A1 | 6/2005 | Straub | |

FOREIGN PATENT DOCUMENTS

| | | | |
|---|---|---|---|
| CA | 2254579 | 6/1999 | |
| GB | 2293380 | 3/1996 | |
| JP | 8505151 A1 | 6/1996 | |
| WO | 86/07590 A1 | 12/1986 | |
| WO | 94/21603 A1 | 9/1994 | |
| WO | 95/24403 A1 | 9/1995 | |
| WO | 02/02378 | 1/2001 | |
| WO | WO 0102378 A1 * | 1/2001 | .......... C07D 277/36 |
| WO | 01/66529 | 9/2001 | |
| WO | 02/06256 A1 | 1/2002 | |
| WO | 02/06257 A1 | 1/2002 | |
| WO | 02/06259 | 1/2002 | |
| WO | 02/06259 A1 | 1/2002 | |
| WO | 02/06260 A1 | 1/2002 | |
| WO | 03/059896 A1 | 7/2003 | |

OTHER PUBLICATIONS

Patani et al. "Bioisosterism: A Rational Approach in Drug Design" Chemical Reviews 1996, vol. 96, pp. 3147-3176.*
Betterton "Oxidation of Alkyl Sulfides by Aqueous Peroxymonosulfate" Environ. Sci. Technol., 1992, vol. 26, pp. 527-532.*
Tetrahedron 57, (month unavailable) 2001, pp. 2469-2476, Kazuhiko Sato et al, Oxidation of sulfides to sulfoxides and sulfones with 30% hydrogen peroxide under organic solvent- and halogen-free conditions.
Spec. Publ.—R. Soc. Chem. 260, (month unavailable) 2001, pp. 47-53, David A Jackson et al, "Sulphones by Oxidation—The Development Perspective".
Synthesis, No. 4, (month unavailable) 1999, pp. 507-509, John Leonard et al, "A Practical Large-Scale Synthesis of 3-Carbomethoxy-3-sulfolene".
Tetrahedron Lett., 35, (month unavailable) 1994, pp. 3457-3460, Kevin S. Webb, "A Mild, Inexpensive and Practical Oxidation of Sulfides".
Tetrahedron Lett., 38, (month unavailable) 1997, pp. 5873-5876, Paul Johnson et al, "The First Preparation of Episulfones from Episulfides: Oxidation Using Oxone®/Trifluoroacetone".
Joule, "1,3-Azoles: General Discussion and a Comparison with Pyrrole, Thiophen and Furan and also with Pyridine", Heterocyclic Chemistry (1972), pp. 299-320, Van Nostrand Reinhold Company, London.
Qui, Zhan, "Sell Oxone, Virkon, Caroat, Potassium, Monopersulfate", http://www.fuzing.com, Copyright © 2003-2009.
"Potassium Peroxymonosulfate", http://en.wikipedia.org/wiki/potassium_peroxymonosulfate (last visited on Dec. 9, 2009 and last modified on Apr. 26, 2009) Wikipedia®, Wikimedia Foundation, Inc.
"Caroat", http://www.ansinchem.com/Caroat (last visited on Dec. 9, 2009) Copyright © 2006, Shanghai Ansin Chemical Co., Ltd.
English Translation of JP Patent Application No. 2004-518547 Final Rejection mailed Jun. 29, 2010.

(Continued)

*Primary Examiner* — Joseph Kosack
(74) *Attorney, Agent, or Firm* — Browdy and Neimark, PLLC

(57) ABSTRACT

The present invention relates to a process for preparing heterocyclic fluoroalkenyl sulfones and fluoroalkenyl sulfoxides by allowing the corresponding fluoroalkenyl thioethers to react with a salt of peroxomonosulfuric acid ($H_2SO_5$), optionally in the presence of a reaction assistant and optionally in the presence of a diluent.

9 Claims, No Drawings

(56) References Cited

OTHER PUBLICATIONS

English Translation of Appeal Brief in corresponding Japanese Application No. 2004-518547 on Dec. 24, 2010 and amended on Feb. 8, 2011.

Ball, D. et al., "THe Kinetics and Mechanism of the Decomposition Caro's Acid", The Journal of the American Chemical Society, vol. 78, pp. 1125-1129 (1956).

Betterton, E., "Kinetics and Mechanism of the Oxidation of Aqueous Hydrogen Sulfide by Peroxymonosulfate", Environmental Science Technology, vol. 24, pp. 1819-1824 (1990).

Betterton, E. et al., "Oxidation of Aqueous SO2 by Peroxymonosulfate", The Journal of Physical Chemistry, vol. 92, pp. 5962-5965 (1988).

Dupont Oxone, Monopersulfate Compound Technical Information, p. 4, lines 2-5, 1998.

Kennedy, R., et al., "The Oxidation Substances by Potassium Peroxymonosulfate", Journal of Organic Chemistry, vol. 25, pp. 1901-1906 (1960) XP-001155253.

Spiro, M., "The Standard Potential of the Peroxosulphate/Sulphate Couple", Electrochimica ACTA, vol. 24, pp. 313-314 (1979).

Trost et al., "Chemoselective Oxidation Sulfides to Sulfphones With Potassium Hydrogen Persulfate", vol. 22, No. 14, pp. 1287-1290 (1981) XP0090138367.

* cited by examiner

METHOD FOR PRODUCING HETEROCYCLIC FLUOROALKENYL SULFONES

The present patent application has been filed under 35 U.S.C. 371 as a national stage application of PCT/EP2003/006511, filed Jun. 20, 2003, which was published in German as International Patent Publication WO 2004/005268 on Jan. 15, 2004, which is entitled to the right of priority of German Patent Application 102 29 776.2, filed Jul. 3, 2002.

The present invention relates to a process for preparing heterocyclic fluoroalkenyl sulfones and fluoroalkenyl sulfoxides from the corresponding fluoroalkenyl thioethers.

Heterocyclic fluoroalkenyl sulfones, for example 5-chloro-2-[(3,4,4-trifluoro-3-butenyl)sulfonyl]-1,3-thiazole, which are described as pesticides, for example, in WO 01/02378, U.S. Pat. Nos. 3,513,172, 3,697,538 or WO 95/24403 have hitherto been prepared in 75% yield generally by the oxidation of the thioether with hydrogen peroxide/glacial acetic acid at 55-60° C./6 h (cf., for example, WO 01/02378). The oxidation of the sulfide to the sulfone proceeds in two steps. In the first step, the sulfide (the thioether) is oxidized to the sulfoxide. In the second step, the sulfoxide is in turn oxidized to the sulfone.

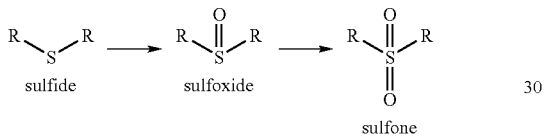

The oxidation of the sulfide to the sulfoxide by the known processes proceeds relatively readily. However, the further oxidation of the sulfoxide to the sulfone takes place only gradually and sluggishly and requires energetic conditions, for example elevated temperature and prolonged reaction times, in the course of which distinct and undesired yield losses may occur as a result of decomposition and side reactions.

The use of the customary oxidation processes known hitherto using hydrogen peroxide and also optionally formic or acetic acid, optionally in the presence of molybdate or tungstate catalysts (EP-A1-0 926 143; U.S. Pat. Nos. 5,965,737; 6,031,108; *Tetrahedron* (2001), 57, 2469; *Spec. Publ.—R. Soc. Chem.* (2001), 260, 47) generally led in particular to the undesired oxidation of the double bond of the halogenated butenyl radical and to its oxidative degradation. Moreover, they harbor considerable explosion risks.

It is therefore an object of the present invention to provide a process for the oxidative preparation of halogenated 2-(3-butenylsulfonyl)-1,3-thiazoles from their sulfides, which prevents the yield losses by decomposition and side reactions, for example the oxidation of the double bond of the butenyl radical, and additionally to develop a process for preparing the desired compounds which is not associated with safety risks.

It has now been found that, surprisingly, the use of salts of peroxomonosulfuric acid of the formula $H_2SO_5$, for example potassium hydrogenperoxomonosulfate, $KHSO_5$, as oxidizing agents allows the use of particularly mild conditions. It has been found that, for example, Oxone® and Caroat® are particularly suitable. It is also to be regarded as surprising that the second step of the oxidation of the sulfoxide to the sulfone, after neutralization of the mixture, proceeds with just as few problems as the first. It is to be regarded as unexpected in particular that it was not possible to observe any significant oxidation of the double bond of the trifluorobutenyl radical, which is particularly problematic in the existing processes.

The present invention therefore provides a process for preparing compounds of the of the formula (I)

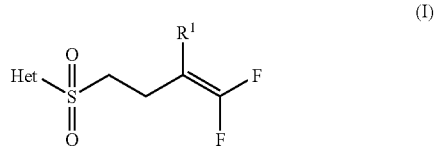

where $R^1$ is hydrogen or fluorine, and

Het is a heterocycle from the following group of heterocycles:

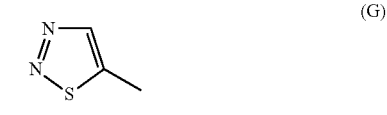

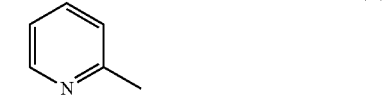

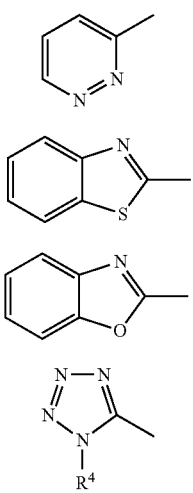

(K)

(L)

(M)

(N)

where
R² is hydrogen, halogen, C₁-C₄-alkyl or C₁-C₄-haloalkyl,
R³ is hydrogen, halogen, and also optionally halogen-, methyl-, ethyl-, n- or i-propyl- or n-, i-, s- or t-butyl-, methoxy-, ethoxy-, n- or i-propoxy- or n-, i-, s- or t-butoxy-substituted C₁-C₄-alkyl, C₁-C₄-alkoxy, C₁-C₄-alkylthio, C₁-C₄-alkylsulfinyl, C₁-C₄-alkylsulfonyl, C₁-C₄-alkoxycarbonyl, C₁-C₄-alkoxy-C₁-C₄-alkyl, C₁-C₄-alkylthio-C₁-C₄-alkyl, carboxyl, C₁-C₄-alkylaminocarbonyl, C₃-C₆-cycloalkylaminocarbonyl, C₁-C₄-dialkylaminocarbonyl, C₂-C₄-alkenyl, C₂-C₄-alkenylthio, C₂-C₄-alkenylsulfinyl or C₂-C₄-alkenylsulfonyl,
R⁴ is C₁-C₈-alkyl, C₂-C₆-alkenyl, C₁-C₄-haloalkyl, C₁-C₄-alkoxy-C₁-C₄-alkyl, C₁-C₄-alkylthio-C₁-C₄-alkyl, C₃-C₈-cycloalkyl or optionally halogen-, C₁-C₄-alkyl-, C₁-C₄-alkoxy-, C₁-C₄-alkylthio- or C₁-C₄-haloalkyl-substituted phenyl or benzyl,
p is 1, 2 or 3,
X is oxygen or sulfur, and
Y is optionally singly or doubly, identically or differently substituted methylene, and examples of substituents include: in each case optionally halogen-, C₁-C₄-alkoxy-, C₁-C₄-alkylthio-, C₁-C₄-haloalkoxy- or C₁-C₄-haloalkylthio-substituted C₁-C₄-alkyl, C₂-C₄-alkenyl or C₂-C₄-alkynyl, and also optionally singly to triply, identically or differently substituted phenyl, and examples of substituents include: halogen, cyano, nitro, C₁-C₄-alkyl, C₁-C₄-alkoxy, C₁-C₄-alkylthio, C₁-C₄-haloalkyl, C₁-C₄-haloalkoxy or C₁-C₄-haloalkylthio,
by allowing a compound of the formula (III)

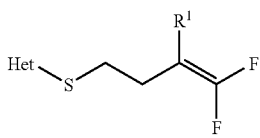

(III)

where
R¹ and Het are each as defined above
to react with a salt of peroxomonosulfuric acid, H₂SO₅, optionally in the presence of a reaction assistant and optionally in the presence of a diluent.

Preferred definitions of the compounds of the formula (I) which are prepared by the process according to the invention are specified hereinbelow:
R¹ is preferably fluorine.
Het is preferably a heterocycle from the following group of heterocycles:

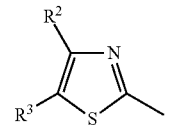
(A)

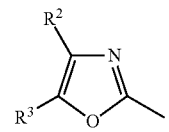
(B)

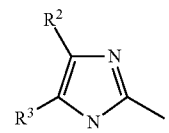
(C)

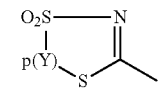
(D)

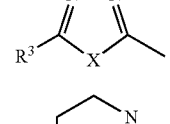
(E)

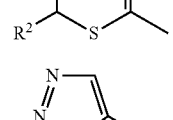
(F)

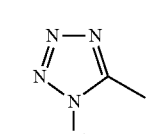
(G)

(N)

R² is preferably hydrogen, fluorine or chlorine.
R³ is preferably hydrogen, fluorine, chlorine, and also optionally fluorine-, chlorine-, methyl-, ethyl-, n- or i-propyl- or n-, i-, s- or t-butyl-, methoxy-, ethoxy-, n- or i-propoxy- or n-, i-, s- or t-butoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulfinyl, ethylsulfinyl, methylsulfonyl, ethylsulfonyl, methoxycarbonyl, ethoxycarbonyl, n- or i-propoxycarbonyl, n-, i-, s- or t-butoxycarbonyl, methoxymethyl, methoxyethyl, ethoxymethyl, ethoxyethyl, methylthiomethyl, methylthioethyl, ethylthiomethyl, ethylthioethyl, carboxyl, methylaminocarbonyl, ethylaminocarbonyl, n- or i-propylaminocarbonyl, cyclopropylaminocarbonyl, cyclobutylaminocarbonyl, cyclopentylaminocarbonyl, cyclohexylaminocarbonyl, dimethylaminocarbonyl, diethylaminocarbonyl, ethenyl, propenyl or butenyl.

R⁴ is preferably methyl, ethyl, n-propyl, isopropyl, n-butyl, isobutyl, tert-butyl, n-pentyl, cyclopropyl, cyclopentyl, cyclohexyl, 2-chloroethyl, 2,2,3,3,3-pentafluoropropyl, 2,2,2-trifluoroethyl, 3-bromopropyl, 2-methoxyethyl, 2-ethoxyethyl, 2-methylthioethyl, allyl, 2-butenyl or in each case optionally singly or doubly, identically or differently fluorine-, chlorine-, bromine-, methyl-, ethyl-, isopropyl-, trifluoromethyl-, methoxy- or methylthio-substituted phenyl or benzyl.

p is preferably 1 or 2.

X is preferably oxygen.

Y is preferably optionally singly or doubly, identically or differently substituted methylene, and examples of substituents include: methyl, ethyl, or optionally singly or doubly, identically or differently substituted phenyl, and examples of substituents include: fluorine, chlorine, methyl, methoxy, trifluoromethyl, cyano or nitro.

Het is more preferably a heterocycle from the following group of heterocycles:

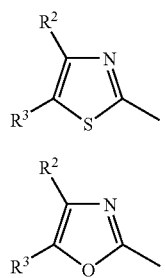

R² is more preferably hydrogen.

R³ is preferably hydrogen, fluorine or chlorine.

p is more preferably 1.

Y is more preferably optionally singly or doubly, identically or differently methyl- or ethyl-substituted methylene, or optionally singly or doubly, identically or differently, fluorine-, chlorine-, methyl-, methoxy-, trifluoromethyl-, cyano- or nitro-substituted phenyl.

Het is most preferably the following heterocycle:

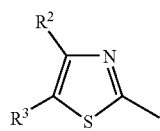

R³ is most preferably chlorine.

The process according to the invention can be illustrated schematically, for example, as follows:

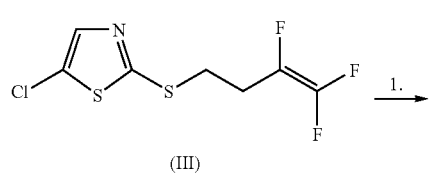

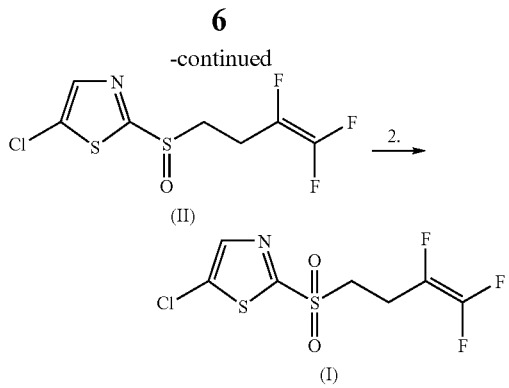

The process according to the invention leads to higher yields, in that the desired product crystallizes out of the reaction mixture after the workup without further purification. Distillation or chromatography is no longer necessary, which likewise has an advantageous effect on the yield.

The inventive process steps may each be carried out in direct succession or else each individually, in which case the particular product may also be purified. Preference is given to using the process according to the invention in order to prepare the sulfones of the formula (I) starting from sulfides of the formula (III).

The process according to the invention may equally be used to prepare sulfoxides of the formula (II)

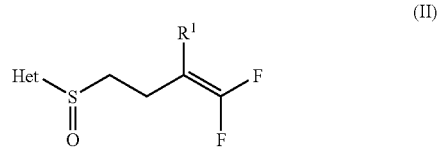

where R¹ and Het are each as defined above
from compounds of the formula (III). In this case, care has to be taken that the pH during the oxidation of the sulfide to the sulfoxide is kept at from 1 to 3.

Equally, the process according to the invention may be used to prepare compounds of the formula (I) from compounds of the formula (II). Here, a pH of from 6 to 10, preferably from 8 to 9, is required (cf. preparation example).

For the preparation of the sulfone from the sulphide, the process according to the invention entails, after the oxidation to the sulfoxide in a first step, an increase during the reaction in the pH which should be from 6 to 10, preferably from 8 to 9 (pH monitoring). The pH may be increased by adding base either after the first step (preparation of the sulfoxide) has been carried out or even during the addition of the first portion of the potassium salt or of the Oxone® to the sulfide (cf. also preparation example).

The bases used may be all common alkali metal and alkaline earth metal hydroxides or alkali metal and alkaline earth metal carbonates, amines, etc. Preference is given to using NaOH, KOH, K₂CO₃ or Na₂CO₃. Particular preference is given to using NaOH.

Any peroxides present in the reaction mixture should be destroyed during the workup for safety reasons. It is therefore important to check for the absence of peroxides in the course of the workup, for example using a Perex Test®.

The compounds used in the process according to the invention to prepare the compounds of the formula (I) and of the formula (II) are characterized generally by the formulae (II) and (III). The compounds of the formula (II) and (III) in which $R^1$ is fluorine are known compounds and are described, for example in WO 95/24403, WO 01/02378, WO 01/66529, WO 02/06259, WO 02/06257, WO 02/06256 and WO 02/06260, and may be prepared, for example, by the processes specified there.

Compounds of the formula (II) and (III) in which $R^1$ is H, are described, for example, in WO 95/24403 and may be prepared by the process specified there.

The preferred salt of peroxomonosulfuric acid used is potassium hydrogenperoxomonosulfate, $KHSO_5$ (CAS-RN 10058-23-8). $KHSO_5$ is used in its stable form as the triple salt of the formula 2 $KHSO_5.KHSO_4.K_2SO_4$ (5:3:2:2) (CAS-RN 70693-62-8). Special preference is given to using Oxone® or Caroat®, in the process according to the invention, particular emphasis being given to Oxone®, as the oxidizing agent.

Oxone® is known to be an oxidizing agent for sulfides (for example R. J. Kennedy, A. M. Stock, *J. Org. Chem.* (1960), 25, 1901; J. Leonard et al., *Synthesis* (1999), 507; K. S. Webb, *Tetrahedron Lett.* (1994), 35, 3457). For example, it has been possible to oxidize episulfides using Oxone® to episulfones ("The First Preparation of Episulfones from Episulfides: Oxidation Using Oxone®/Tetrafluoroacetone", P. Johnson and J. K. Tailor, *Tetrahedron Lett.* (1997) 38, 5873).

The active component of Oxone® is the aforementioned potassium hydrogen-peroxomonosulfate, $KHSO_5$, $[K^+ \phantom{}^-O—S(=O)_2(—OOH)]$, also known as potassium monopersulfate, which is obtainable as the triple salt of the formula 2 $KHSO_5.KHSO_4.K_2SO_4$ (5:3:2:2), for example under the trade names mentioned, Caroat® or Oxone®. The monopotassium salt is used, for example, as a bleach and oxidizing agent in detergents.

The process according to the invention for preparing the compounds of the general formula (I) or of the general formula (II) is preferably carried out using diluents. Useful diluents for carrying out the process according to the invention, in addition to water, are in particular water-miscible solvents, for example ketones such as acetone; nitriles such as acetonitrile, propionitrile or butyronitrile; alcohols such as methanol, ethanol, n- or isopropanol, ethylene glycol monomethyl ether, ethylene glycol monoethyl ether, diethylene glycol monomethyl ether, diethylene glycol monoethyl ether, carboxylic acids such as formic acid, glacial acetic acid or mixtures thereof, ethers such as tetrahydrofuran or dioxane, but equally water-immiscible, inert organic solvents, in which case phase transfer catalysts have to be present. These include aliphatic, alicyclic or aromatic, optionally halogenated hydrocarbons, for example benzine, benzene, toluene, xylene, chlorobenzene, dichlorobenzene, butanone or methyl isobutyl ketone; petroleum ether, hexane, cyclohexane, dichloromethane, chloroform, carbon tetrachloride; ethers such as diethyl ether, diisopropyl ether, 2-methyltetrahydrofuran, methyl t-butyl ether or ethylene glycol dimethyl ether or ethylene glycol diethyl ether; esters such as ethyl acetate or isopropyl acetate. Preferred water-miscible solvents are acetonitrile, acetone, alcohols, especially methanol, ethanol, n- or isopropanol, dioxane, tetrahydrofuran or the abovementioned carboxylic acids. A preferred water-immiscible solvent is, for example, toluene in the presence of a phase transfer catalyst. Particular preference is given to using the alcohols mentioned as solvents.

Useful phase transfer catalysts are, for example, tetrabutylammonium bromide, tetrabutylammonium chloride, tetraoctylammonium chloride, tetrabutylammonium hydrogensulfate, methyltrioctylammonium chloride, hexadecyltrimethylammonium chloride, hexadecyltrimethylammonium bromide, benzyltrimethylammonium chloride, benzyltriethylammonium chloride, benzyltrimethylammonium hydroxide, benzyltriethylammonium hydroxide, benzyltributylammonium chloride, benzyltributylammonium bromide, tetrabutylphosphonium bromide, tetrabutylphosphonium chloride, tributylhexadecylphosphonium bromide, butyltriphenylphosphonium chloride, ethyltrioctylphosphonium bromide, or tetraphenylphosphonium bromide. Especially useful are the particular hydrogensulfates of the phase transfer catalysts.

The reaction may be carried out within a relatively large temperature range, preferably at temperatures between −20° C. and 150° C. Preference is given to using temperatures between 0° C. and 40° C. Preferred temperature ranges may also be taken from the preparation examples.

The pH has to be selected with a view to the particular end product desired (sulfoxide or sulfone). For the preparation of the sulfoxide from the sulfide, the pH should be between 1 and 3. For the preparation of the sulfone from the sulfoxide, the pH has to be increased to from 6 to 10. It is preferably from 8 to 9. The pH may also be increased by adding base even during the addition of the first portion of the Oxone® solution when the sulfide is to be converted to the sulfone.

The processes according to the invention are generally carried out under atmospheric pressure. However, it is also possible to carry out the processes according to the invention under elevated or reduced pressure, generally between 0.1 bar and 50 bar, preferably between 1 and 10 bar.

When the process according to the invention is carried out, to prepare one mole of a compound of the formula (I), preference is given to using at least one mole of a compound of the formula (III) and at least 2 mol of a salt of peroxomonosulfuric acid. The Oxone® may, for example, depending on the temperature, be used in the form of an up to 25-35% aqueous solution.

The workup is carried out by customary methods (cf. the preparation examples).

In a preferred embodiment of the process according to the invention, the compounds of the formula (I) and (II) are prepared by stirring a compound of the formula (III) in solvent, preferably in one of the aforementioned solvents, especially preferably an alcohol, after slowly adding an aqueous solution of potassium hydrogenperoxomonosulfate, preferably Oxone®. Subsequently, the pH is adjusted, preferably using NaOH, to preferably from 8 to 9, and an aqueous solution of potassium hydrogenperoxomonosulfate, preferably Oxone®, is again added and the mixture is stirred further for a certain time, in the course of which the pH is still kept at from 8 to 9. Subsequently, the salts are filtered off with suction and the desired product is purified by customary methods.

The preparation of compounds of the formula (I) or of compounds of the formula (II) is evident from the example which follows, which further illustrates the above-described process steps. However, the example is not to be interpreted in a restrictive manner.

EXAMPLES

Example 1

Preparation of 5-chloro-2-[(3,4,4-trifluoro-3-butenyl) sulfonyl]-1,3-thiazole 26 g (0.1 mol) of 5-chloro-2-[(3,4,4-trifluoro-3-butenyl) sulfanyl]-1,3-thiazole are initially charged in 250 ml of methanol and a solution of 33.9 g of Oxone® in 125 ml of water is added dropwise with stirring at 5° C. within 30 minutes. Subsequently, the white suspension is stirred at 20° C. for 1.5 hours. To complete the first reaction stage (preparation of the sulfoxide), 1.7 g of Oxone® are added once again and the mixture is stirred for a further 30 minutes.

Subsequently, the mixture is cooled back to 5° C., a pH of 8-9 is established using 4 N NaOH and a solution of 33.9 g of Oxone in 125 ml of water is added dropwise within 30 minutes, in the course of which the pH is still kept at 8-9. The total consumption of 4 N NaOH is approx. 70 ml (2.54 equivalents based on Oxone®). Subsequently, the mixture is stirred with pH monitoring at 20° C. for 60 minutes, then 1 g of Oxone® is added once again and the mixture is stirred for a further 20 minutes.

The salts are filtered off with suction, the white residue is washed twice with 30 ml each time of methanol, and the filtrate is stirred with 25 ml of sodium bisulfite solution and tested for peroxides. The methanol fraction is then distilled off from the filtrate under reduced pressure. The organic phase is removed from the aqueous, biphasic residue and the aqueous phase is again extracted three times with ethyl acetate. The combined organic phases are tested for peroxide, dried over sodium sulfate and concentrated by evaporation. 27.6 g (92.2% of theory) of a yellowish oil are obtained which, after scratching and cooling, crystallizes and has a melting point of 34° C. The content (HPLC against standard) is 97.6%.

What is claimed is:

1. A process for preparing a heterocyclic fluoroalkenyl sulfone compound of formulas (I)

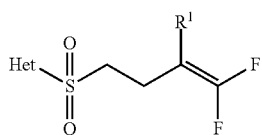

(I)

where
$R^1$ is hydrogen or fluorine, and
Het is a heterocycle selected from the group consisting of

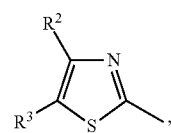

(A)

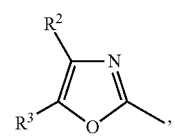

(B)

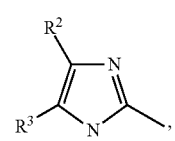

(C)

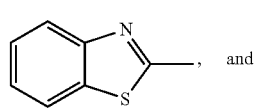

(L)

, and

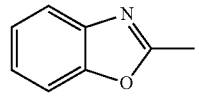

(M)

where
$R^2$ is hydrogen, halogen, $C_1$-$C_4$-alkyl, or $C_1$-$C_4$-haloalkyl, and
$R^3$ is hydrogen or halogen; or is optionally halogen-, methyl-, ethyl-, n- or i-propyl-, n-, i-, s-, or t-butyl-, methoxy-, ethoxy-, n- or i-propoxy-, or n-, i-, S-, or t-butoxy-substituted $C_1$-$C_4$-alkyl, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_4$-alkoxycarbonyl, $C_1$-$C_4$-alkoxy-$C_1$-$C_4$-alkyl, $C_1$-$C_4$-alkylthio-$C_1$-$C_4$-alkyl, carboxyl, $C_1$-$C_4$-alkylaminocarbonyl, $C_3$-$C_6$-cycloalkylaminocarbonyl, $C_1$-$C_4$-dialkyl-aminocarbonyl, $C_2$-$C_4$-alkenyl, $C_2$-$C_4$-alkenylthio, $C_2$-$C_4$-alkenylsulfinyl, or $C_2$-$C_4$-alkenylsulfonyl, comprising:
allowing a sulfide compound of formula (III)

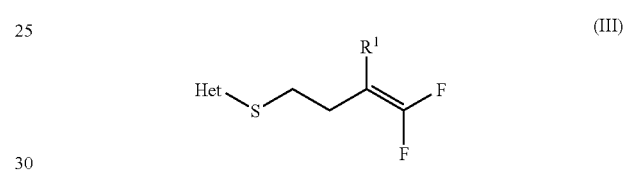

(III)

where $R^1$ and Het are each as defined for formula (I),
to react with a salt of peroxomonosulfuric acid ($H_2SO_5$), in a reaction, optionally in the presence of a reaction assistant and optionally in the presence of a diluent to obtain a sulfoxide compound of formula (II)

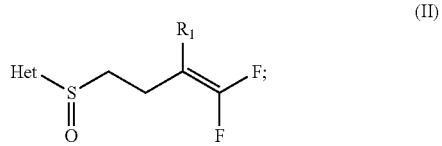

(II)

adjusting the pH to a range of 6 to 10;
after adjusting the pH of the reaction to a range of 6 to 10, adding more salt of peroxomonosulfuric acid to the reaction; and
allowing the resultant sulfoxide compound of formula (II) to react with the salt of peroxomonosulfuric acid at the pH in the range of 6 to 10, optionally in the presence of a reaction assistant and optionally in the presence of a diluent, to produce the sulfone compound of formula (I).

2. A process according to claim 1, wherein a compound of formula (III) is allowed to react with a salt of peroxomonosulfuric acid ($H_2SO_5$), at a pH in a range of 1 to 3, optionally in the presence of a reaction assistant and optionally in the presence of a diluent.

3. A process according to claim 1 in which the salt of peroxomonosulfuric acid is potassium hydrogenperoxomonosulfate (2 $KHSO_5$·$KHSO4$·$K_2SO_4$ (5:3:2:2)).

4. A process according to claim 1 carried out at a temperature in a range of −20° C. to 150° C.

5. A process according to claim 1 in which
$R^1$ is fluorine,

Het is a heterocycle selected from the group consisting of

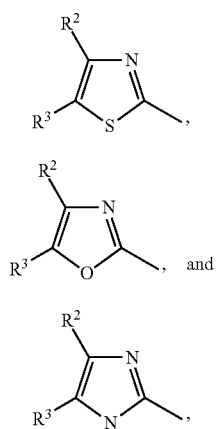

R² is hydrogen, fluorine, or chlorine,
R³ is hydrogen, fluorine, or chlorine; or is optionally fluorine-, chlorine-, methyl-, ethyl-, n- or i-propyl-, n-, i-, S-, or t-butyl-, methoxy-, ethoxy-, n- or i-propoxy-, n-, i-, S-, or t-butoxy-substituted methyl, ethyl, n- or i-propyl, n-, i-, S-, or t-butyl, methoxy, ethoxy, n- or i-propoxy, n-, i-, S-, or t-butoxy, methylthio, ethylthio, n- or i-propylthio, n-, i-, S-, or t-butylthio, methylsulfinyl, ethylsulfinyl, methylsulfonyl, ethylsulfonyl, methoxycarbonyl, ethoxycarbonyl, n- or i-propoxycarbonyl, n-, i-, S-, or t-butoxycarbonyl, methoxymethyl, methoxyethyl, ethoxymethyl, ethoxyethyl, methylthiomethyl, methylthioethyl, ethylthiomethyl, ethylthioethyl, carboxyl, methylaminocarbonyl, ethylaminocarbonyl, n- or i-propylaminocarbonyl, cyclopropylaminocarbonyl, cyclobutylaminocarbonyl, cyclopentylaminocarbonyl, cyclohexylaminocarbonyl, dimethylaminocarbonyl, diethylaminocarbonyl, ethenyl, propenyl, or butenyl.

6. A process according to claim 1 in which Het is a heterocycle selected from the group consisting of

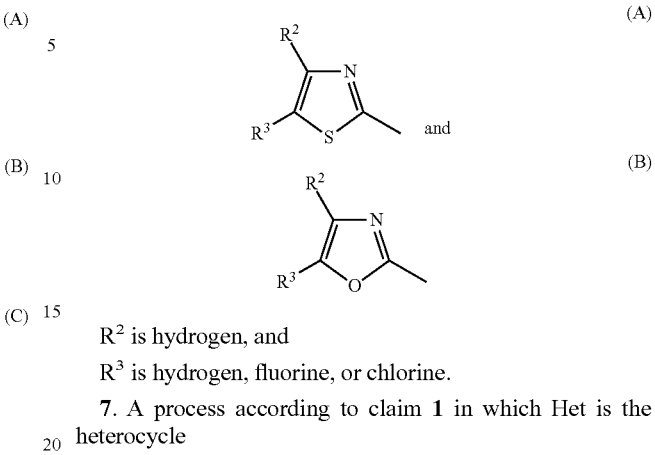

R² is hydrogen, and
R³ is hydrogen, fluorine, or chlorine.

7. A process according to claim 1 in which Het is the heterocycle

R² is hydrogen, and
R³ is chlorine.

8. A process for preparing a compound of formula (I) as defined in claim 1, wherein a compound of formula (II) as defined in claim 1 is allowed to react with a salt of peroxomonosulfuric acid ($H_2SO_5$), optionally in the presence of a reaction assistant and optionally in the presence of a diluent, wherein the process is conducted at a pH of from 6 to 10.

9. The process of claim 1, which is carried out at a temperature in a range of 0° C. to 40° C.

* * * * *